United States Patent [19]

Wentzell et al.

[11] 4,368,644

[45] Jan. 18, 1983

[54] TOOL FOR INSPECTING DEFECTS IN IRREGULAR WELD BODIES

[75] Inventors: Timothy H. Wentzell, South Windsor; Charles B. Innes, Jr., Granby, both of Conn.

[73] Assignee: Combustion Engineering, Inc., Windsor, Conn.

[21] Appl. No.: 267,142

[22] Filed: May 26, 1981

[51] Int. Cl.³ .................. G01N 9/24; G01N 9/04; G01N 29/04; G21C 17/00

[52] U.S. Cl. .................. 73/634; 73/638; 73/623; 73/622; 376/249; 376/252

[58] Field of Search .......... 73/634, 637, 638, 635, 73/623, 633; 376/249, 252

[56] References Cited

U.S. PATENT DOCUMENTS

| | | | |
|---|---|---|---|
| 3,056,285 | 10/1962 | Gibson et al. | 73/638 |
| 3,077,768 | 2/1963 | Allardt et al. | 73/634 |
| 3,182,490 | 5/1965 | Gibson | 73/638 |
| 3,780,571 | 12/1973 | Wiesener | 73/623 |
| 3,789,656 | 2/1974 | Miller | 73/635 |
| 3,862,578 | 1/1975 | Schluter | 376/249 |
| 3,943,756 | 3/1976 | Aubert et al. | 376/249 |
| 4,068,523 | 1/1978 | Hetherington et al. | 73/628 |
| 4,117,733 | 10/1978 | Gugel | 376/249 |
| 4,130,021 | 12/1978 | Mueller et al. | 73/633 |
| 4,130,022 | 12/1978 | Goodrich et al. | 73/633 |
| 4,131,018 | 12/1978 | Müller et al. | 73/623 |
| 4,158,309 | 6/1979 | Elsner et al. | 73/623 |
| 4,233,988 | 11/1980 | Dick et al. | 73/633 |
| 4,238,962 | 12/1980 | Taenzer | 73/633 |
| 4,258,576 | 3/1981 | Vilkomerson et al. | 73/633 |
| 4,274,289 | 6/1981 | Weiss et al. | 73/634 |

OTHER PUBLICATIONS

Mechanized Eq. for Nuclear Reactors, by C. E. Lautzenheizer, Instn. Mech. Eng. 657/72, 1972, Conference on Periodic Inspection of Pressure Vessels, London England May 9–11, 1972.

Primary Examiner—Anthony V. Ciarlante
Assistant Examiner—David V. Carlson
Attorney, Agent, or Firm—Arthur L. Wade

[57] ABSTRACT

A tool for manipulating an ultrasonic inspection transducer is actuated to move the transducer over the surface of an irregular weld body. The weld body disclosed, joins the nozzle of a reactor vessel to its vessel, the irregularity of the weld body defined by the intersection of the two cylinders. The transducer is moved over the surface of the weld body and actuated to scan through a predetermined angle in relation to the changing aspect of the geometry of the weld body by a cam mounted at the pivoting center of the tool.

6 Claims, 6 Drawing Figures

TOOL FOR INSPECTING DEFECTS IN IRREGULAR WELD BODIES

TECHNICAL FIELD

The present invention relates to the manipulation of ultrasonic transducers over the welds of nuclear vessel nozzles. More specifically, the invention relates to articulating sled-mounted ultrasonic transducers to scan the complete weld body joining the nozzle and nuclear vessel wall.

BACKGROUND ART

For a utility operating a nuclear reactor system, it is imperative that Inservice Inspection (ISI) of the reactor system welds be performed as rapidly as possible without sacrificing accuracy. The inspection system is comprised of mechanical positioning equipment and nondestructive examination instrumentation. It is desirable to reduce the time in making these inspections without reducing the quality of the examinations. Reduction in this time will enable the utility to realize savings in operating costs due to shorter downtimes and a reduction in radiation exposure to examination personnel.

The present rules for ISI, established by the ASME Code, Section XI "Rule for Inservice Inspection of Nuclear Power Plant Components", require a complete inspection of reactor vessel welds every ten operational years. In addition, it is a USNRC requirement that personnel radiation exposure be "as low as reasonably achievable." Hence, it is inevitable, based on these criteria and the very high cost of plant downtime, that an inspection agency must provide reliable, accurate, and rapid inspection techniques.

The inservice inspection program includes both the component and piping welds. In general, there are numerous access problems, weld configuration variations and radiation hazards that must be considered. The inservice inspection tool is mounted on the flange of the nuclear vessel and manipulated beneath many feet of radiation-shielding water. The area to be inspected in and about the nuclear vessel is reached with predetermined location information, supplemented by TV cameras. The ISI tool, from its mount on the reactor vessel flange, is capable of reaching all areas of the reactor vessel by actuating rotating and telescoping booms along with specially designed fixtures that hold the ultrasonic search units.

The operating console for this tool contains the necessary controls and instruments for manifesting readout information for both the inspection booms and attachments. The controller allows the operator to move the search units accurately through all the required examination regions and provides precise position data. By enhancing the versatility of the inspection equipment, the number and frequency of mechanical configuration changes can be reduced. This has resulted in a reduction in setup time and, equally important, greatly reduced handling of contaminated parts. This versatility is achieved by means of remote or preprogramed articulation of ultrasonic weld entry angles. The prior art approach to this problem is to use several transducers preset at specific sound angles. This method has the disadvantage of increased size and weight, resulting in an inability to inspect close to obstructions and requiring massive manipulating equipment and changes of sleds on which the transducers are mounted.

Means are needed to remotely and automatically change the transducer angles, enabling the inspection of weld volumes adjacent to obstructions and in areas of complex geometry. This technique will particularly improve the inspection of the reactor vessel nozzle-to-shell weld where the weld configuration has a complex geometry represented by the inspection of two cylinders. In order to perform this examination with the sound angle parallel to the weld centerline, the sound angle must be skewed continuously through a predetermined angle with respect to the vessel surface as the search unit is translated along the weld.

DECLARATION OF THE INVENTION

The present invention contemplates the use of a cam-operated closed-loop hydraulic system to control the sound entry angles of the transducer by articulation of the transducer as the sleds of the transducer traverse the complex surface geometry of the nozzle-to-vessel weld. This closed-loop hydraulic servo system articulates the transducers such that their ultrasonic beam follows the actual weld centerline. By changing the cam, which is actually a preprogrammed scan plan, the welds of different sizes and configurations of nozzles can be inspected.

Other objects, advantages and features of this invention will become apparent to one skilled in the art upon consideration of the written specification, appended claims, and attached drawings.

BRIEF DESIGNATION OF THE DRAWINGS

BEST MODE FOR CARRYING OUT THE INVENTION

Generalizations

Figure 1:
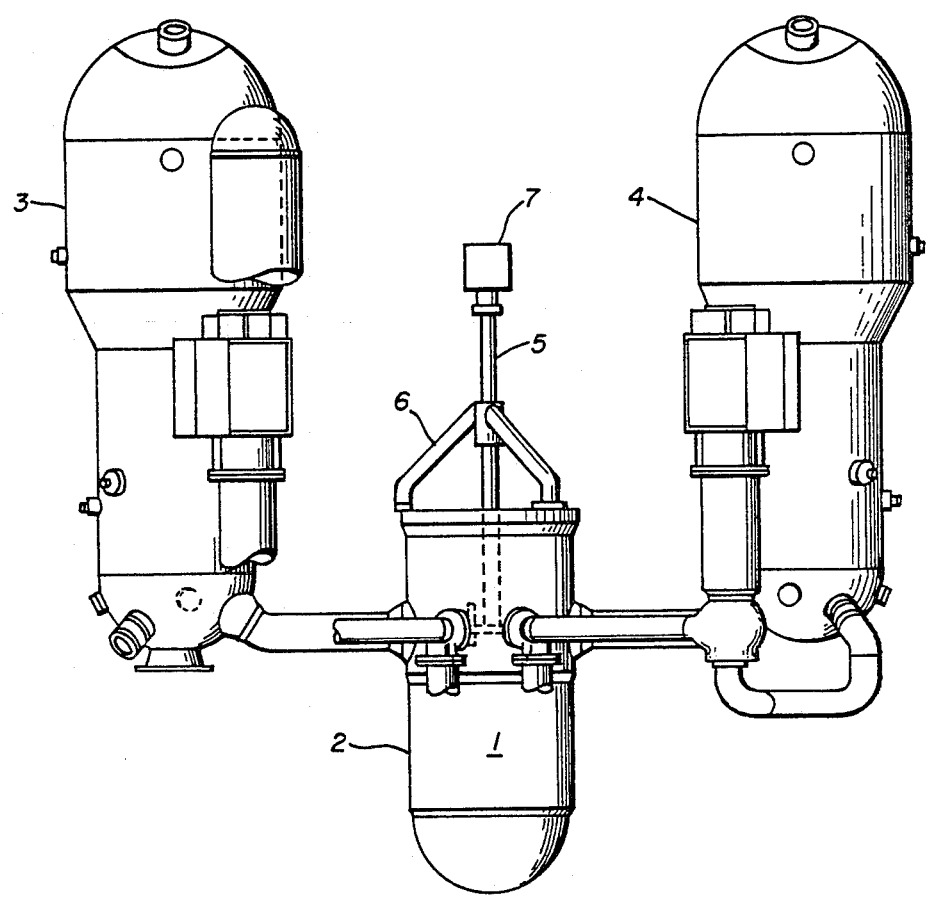
FIG. 1 is a front elevation of steam generators connected to a nuclear reactor vessel whose nozzles are welded to the vessel and inspected by an ultrasonic tool embodying the present invention.

The first three figures of the drawing disclosure show a proper environment for the embodiment of the invention. The present invention is concerned directly with detecting flaws, imperfections, or defects that develop in the weld body connecting the nozzle/conduit through the side of a nuclear reactor vessel. Once the integrity of this weld body fails to a certain point, disaster can strike by the discharge of the radioactive materials from inside the reactor vessel into the containment area. Therefore, the present invention is embodied in an inspection tool which is periodically used to perform the vital function of verifying the structural integrity of the reactor vessel.

FIG. 1 is designed to disclose a reactor vessel with the top cover removed and filled with water. The water is required as an effective shield against radiation. The steam generators are connected to the reactor vessel by conduits, the conduits being connected to the reactor vessel with the welds which require periodic inspection. No specific representation of the water level is delineated. If is sufficient to understand that, during the inspection, the reactor vessel is open at its top but retains enough water to shield personnel from radiation. Therefore, the inspection is carried out under the surface of this shielding water body.

Figure 2:
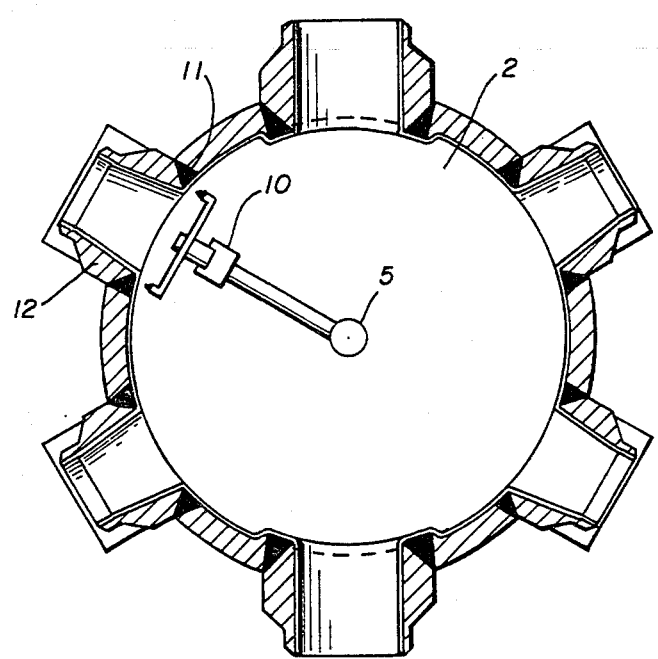
FIG. 2 is a plan view of the nuclear reactor vessel of FIG. 1 disclosing the ultrasonic detection tool being positioned for nozzle-to-vessel weld body inspection.

The personnel, for the present disclosure, may be considered as operating from a platform well above the water shield body, regardless of the height of the body. Although this platform is not shown, FIG. 2 is offered as a sectional view through the reactor vessel and nozzles. The view of FIG. 2 gives observation down into the inside of the reactor vessel. A representation of the inspecting structure in which the present invention is embodied is indicated to further orient the observer. The welds to be inspected are shown as triangles 11.

Figure 3:
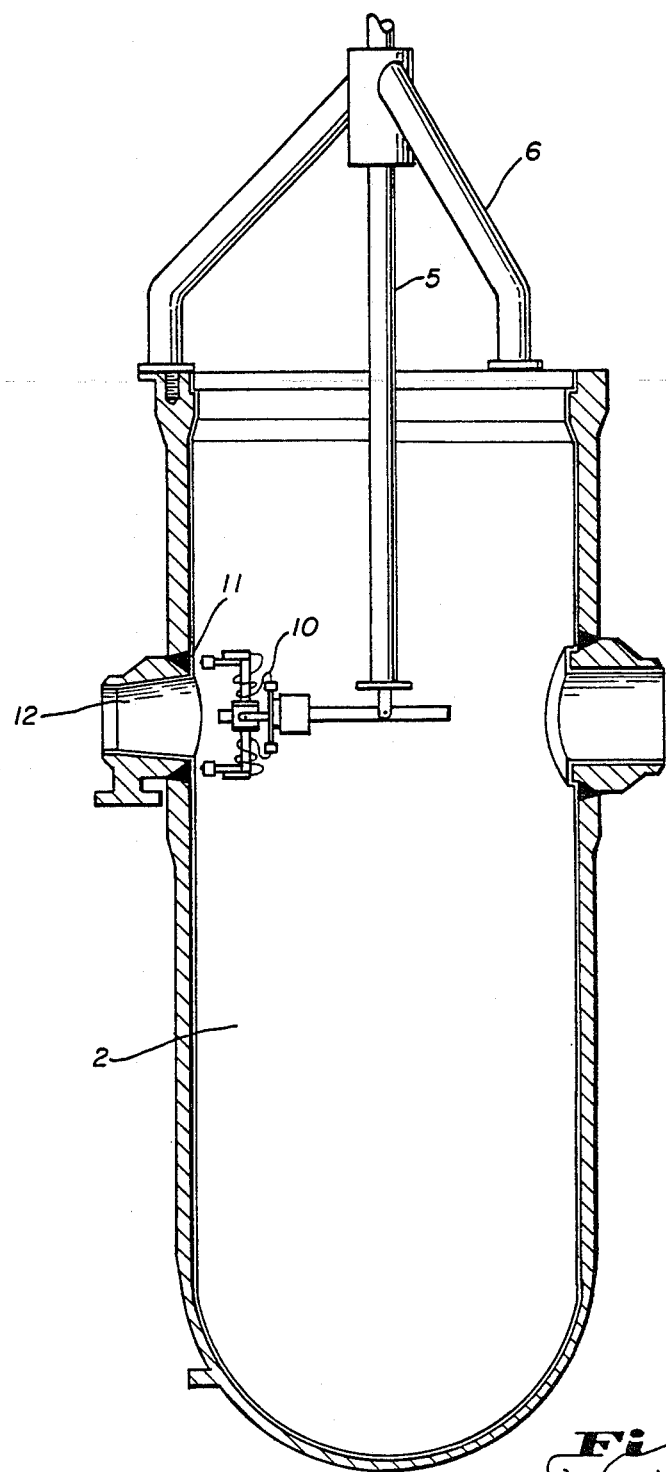
FIG. 3 is a sectioned elevation of the nuclear vessel of FIG. 1 disclosing the nozzle-to-vessel weld body inspected by a tool embodying the present invention.

FIG. 3 is simply a closeup of the reactor vessel in sectioned elevation to project the specific location of the weld to be inspected. The section is made large enough to illustrate the triangular weld shape at 11 and further the awareness of the problem of scanning this weld body by progressing an ultrasonic probe through a circular sweep.

FIG. 1—The Broader View

Of course, the basic purpose of the nuclear reactor is to heat a liquid coolant whose heat is then transferred to a second liquid which is vaporized. Therefore, a radioactive fuel 1 is disclosed positioned within the lower region of vessel 2. In actual operation, a coolant is pumped through this source of heat and into heat exchangers 3 and 4 where the heat of the reactor fuel is transferred to water that will turn to steam, and the coolant is then returned to the reactor to complete a closed loop. It is, of course, imperative that the radioactive material of the nuclear fuel be prevented from escaping into the atmosphere. The uses of steam to generate power are well-known. The present invention is concerned with the complex geometry of the weld bodies which connect the conduits between steam generators 3 and 4 and the reactor vessel.

Each of the conduits connected to the vessel 2 are welded to the vessel by a body of weld material which must be periodically inspected for the development of flaws which may threaten its integrity. As the vessel is scheduled to be opened for fuel replacement, this downtime can be utilized to make the required inspections of the weld bodies.

As the opened vessel 2 is a source of radiation, the inspection must be carried out through remotely-operated mechanical structures from a position within safe environments. The safe environment in the present disclosure is not directly shown. Imagination can be relied upon to visualize a platform for personnel which is located 30 feet or more above reactor vessel 2. From this platform, after the vessel 2 has been opened, an apparatus is extended down to the vessel 2. The apparatus extended down to the vessel is referred to in the art as a PAR (Programed and Remote), being, basically, a boom which telescopes in X and Z axes to bring the inspection apparatus embodying the present invention to the weld bodies to be inspected. The boom 5 of the PAR has a tripod 6 on its lower end which is engaged with the upper flange of the reactor vessel 2. With this tripod as the stabilizing link between the PAR and the reactor vessel, the embodying inspection tool is precisely positioned to the surface of the weld body inspected. All signals to and from the inspection tool are on instrument lines which terminate in a station 7. Station 7 is then connected with control and instrumentation at the platform, not shown.

FIG. 2

The disclosure of FIG. 2 adds a dramatic perspective to the overall task of lowering the inspecting apparatus into the reactor vessel 2. Strategically placed TV cameras (not shown) give guidance in checking the positioning of the inspecting apparatus in vessel 2. Some indication of the weld inspection apparatus is disclosed at 10 as it is supported on the boom of the PAR. Careful measurements are established in original fabrication of vessel 2 so the PAR, on which the instrument is lowered, can be manipulated from the platform. Again, TV cameras supplement the mechanical indices in moving the inspection equipment efficiently.

FIG. 3

Providing this sectioned elevation of vessel 2 adds to the disclosure of FIGS. 1 and 2 by giving location and configuration information to the inspected weld bodies. Therefore, weld body 11 can be seen as having a cross-sectional, triangular shape, the point of the triangle being away from the inside of the nozzle/conduit which the weld body joins to vessel 2. This weld body is a continuous circle of material which follows the intersection of the cylindrical nozzle 12 with the much larger cylindrical wall of vessel 2. It is geometrically obvious that the weld body does not lie in a flat plane, but has the general configuration relative to a plane of any intersection of cylindrical bodies intersecting each other at right angles. The ultrasonic transducer of the weld-inspecting tool must be carried over the inside surface of weld body 11 with a consistent positional relationship to the centerline of the weld body. It is readily apparent that the centerline of this weld body 11 is not constant relative to the surface of the vessel 2 and challenges the invention to move the inspection transducers over the surface of the weld while maintaining a required angle of its output ultrasonic beam relative to the centerline of the weld which varies with respect to the vessel 2 surface from which the inspection is performed.

Figure 4:
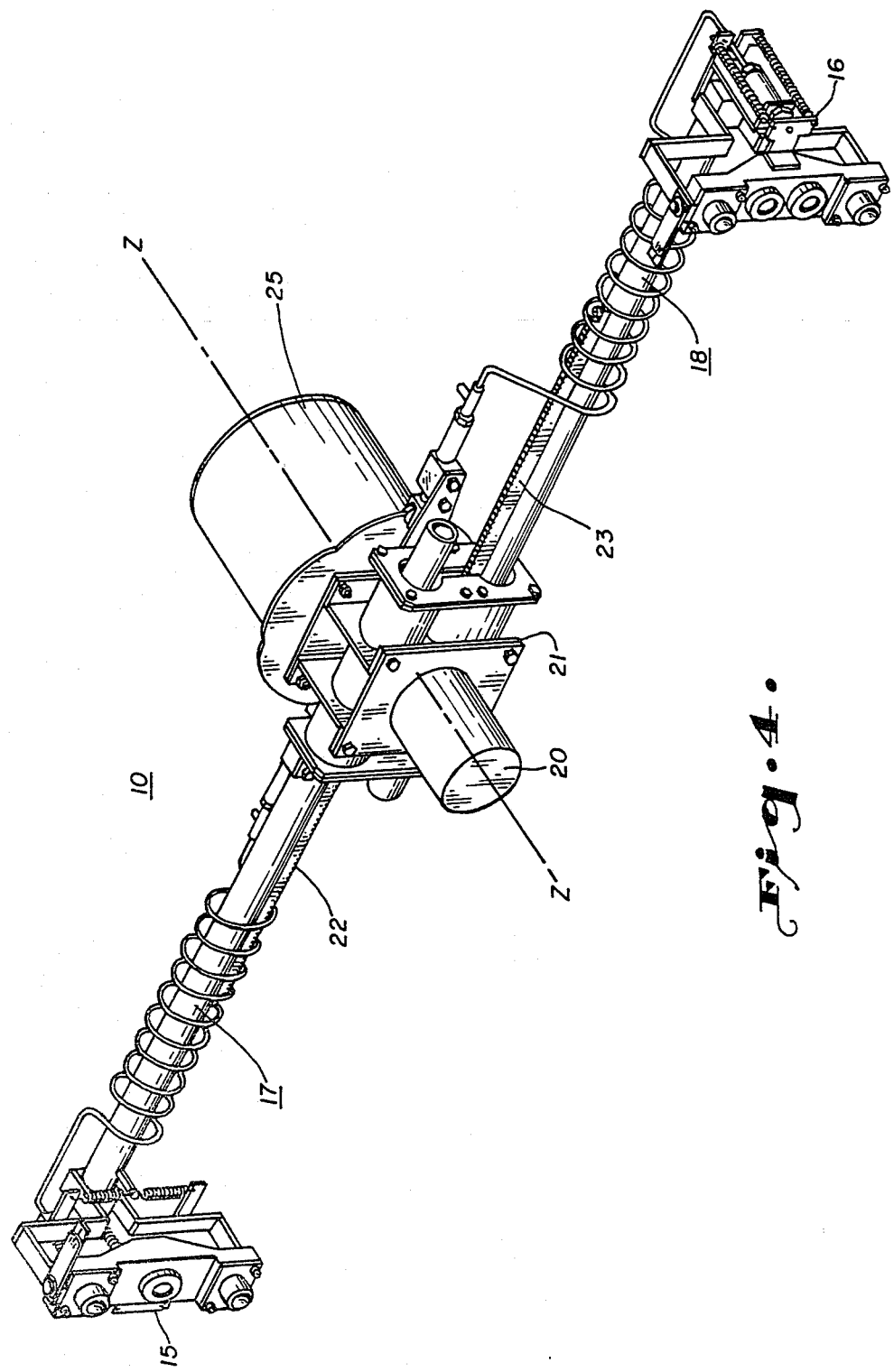
FIG. 4 is an isometric of the inspection tool including the cam-operated closed circuit hydraulic system and associated components.
Figure 5:
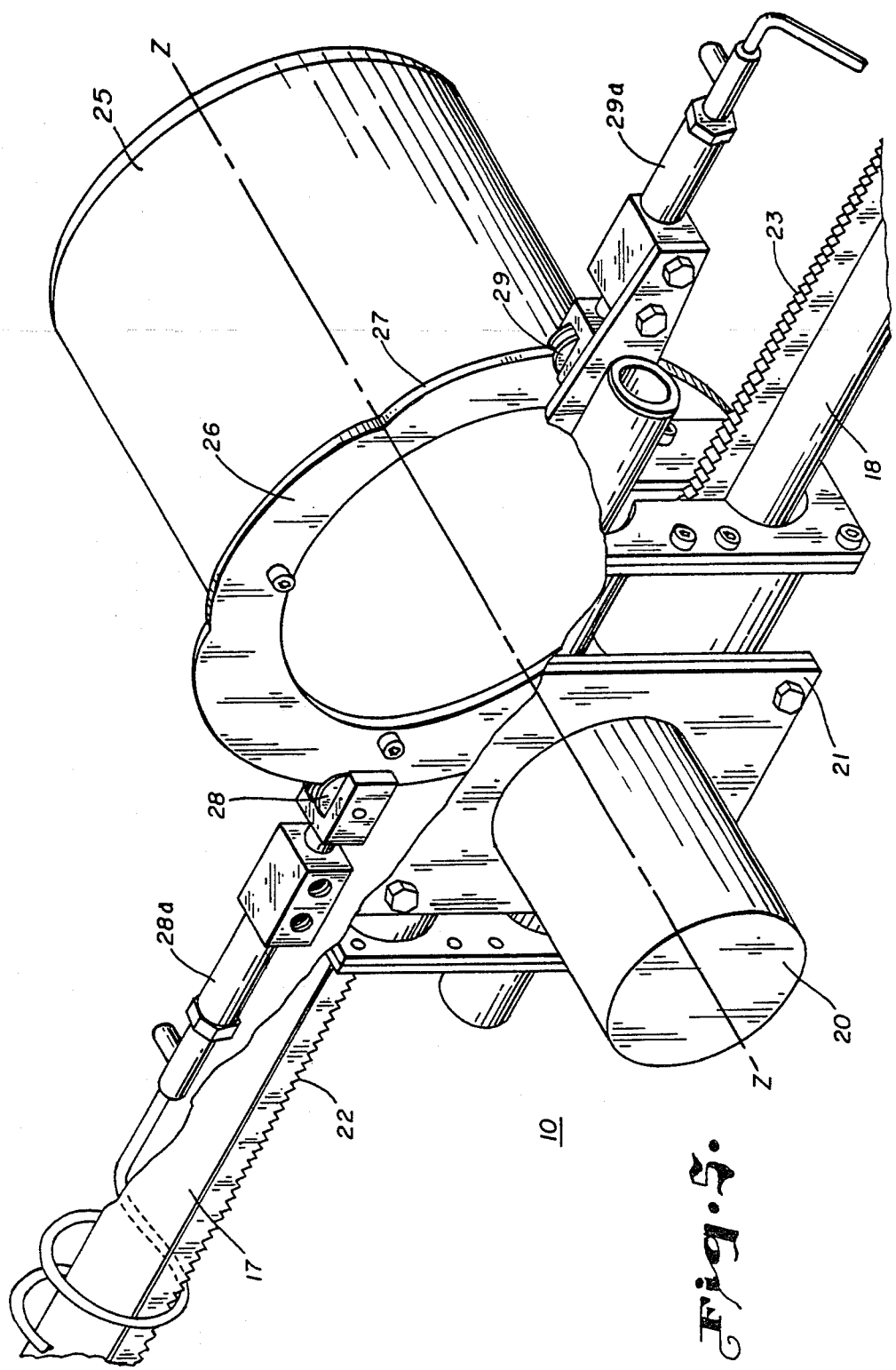
FIG. 5 is a perspective of the central portion of FIG. 4.

FIGS. 4 and 5

The complete inspection tool 10 has been disclosed in FIGS. 2 and 3 as being positioned to inspect weld body 11. In FIGS. 4 and 5, only that part of the complete tool which directly supports and positions the ultrasonic probes is disclosed. The framework with which the disclosed apparatus of FIGS. 4 and 5 is moved and positioned is well-known and need not be disclosed here. The invention is embodied in the structure which automatically changes the positions of the ultrasonic probes at their attachment to the outer ends of the rotating arms of tool 10, and FIGS. 4 and 5 are to be considered together in developing the structure and arrangement of this inventive embodiment.

In FIG. 4, ultrasonic probes, or transducers, at 15 and 16 are mounted on the outer ends of arms 17 and 18. Arms 17 and 18 are rotated about axis Z which hereinafter will be referred to, rather than centerline of nozzle 12. Carried at the outer ends of arms 17 and 18, the probes traverse the surface of weld body 11. While carried over the surface of weld body 11, the probes are articulated by the inventive embodiment through predetermined angles with respect to the vessel surface such that the ultrasonic sound beams maintain a required angle for proper flaw detection.

It is necessary to extend and retract the ends of arms 17 and 18, relative to axis Z, to obtain proper inspection area coverage. A motor 20 is mounted at axis Z on bearing housing 21 and linked to arms 17 and 18 for the purpose of controlling the distance of the outer ends of the arms from axis Z.

As the drawing arrangement precludes convenient disclosure of a pinion gear on the shaft of motor 20, it remains with the mechanical perception of one skilled in the art to understand that this pinion gear engages a toothed rack which is a part of each arm. As the pinion gear is rotated by motor 20, it simultaneously engages racks 22 and 23. It is then obvious that this engagement between racks and pinion gear will extend or retract arms 17 and 18 as motor 20 is rotated clockwise or counterclockwise.

The extending and retracting of the arms is necessary for the probes at 15 and 16 to inspect the full width of the circular weld path. A complete inspection consists of several concentric sweeps by the probes. A first program to control motor 20 is established in a procedure well-known in the prior art. Therefore, in summation to this point in the disclosure, the arms 17 and 18 are positioned along axis Z and retracted or extended as required to inspect the weld body volume. The probes at 15 and 16 are carried over the surface of weld body 11 in a consistent relationship with the centerline of the weld body 11. The inventive embodiment then articulates the probes at 15 and 16 to direct their outputs into the body of the weld 11 at angles relative to the weld centerline to insure plenary scanning of the weld body in search of flaws.

FIG. 5 shows the structure enlarged at the center of arm rotation to more clearly disclose the inventive embodiment which articulates the probes at 15 and 16. Motor housing 25 is fixed to the horizontal arm of the PAR. The output shaft of this motor is fixed to bearing housing 21. Thus, motor housing 25 does not rotate. However, bearing housing 21 and all parts attached thereto do rotate about axis Z. The inventive structure is dominated by cam 26. Cam 26 is disclosed as in a plane normal to axis Z and nested between motor housing 25 and bearing housing 21. Mounted on motor housing 25, cam 26 applies the contours of its outer edge 27 to followers 28 and 29. The follower 28 is mounted on housing 21 and the follower 29 is also mounted on housing 21. As arms 17 and 18 are rotated about axis Z, the followers rise and fall by the configuration of cam profile 27.

With the contours of the profile 27 of cam 26 establishing their predetermined movement of followers 28 and 29, there remains only the linking of this movement to the articulation of the probes at 15 and 16. The invention provides a closed loop hydraulic system mounted on the bearing housing 21 and on the arms to include these cam followers as the link between the probes and cam 26.

Figure 6:
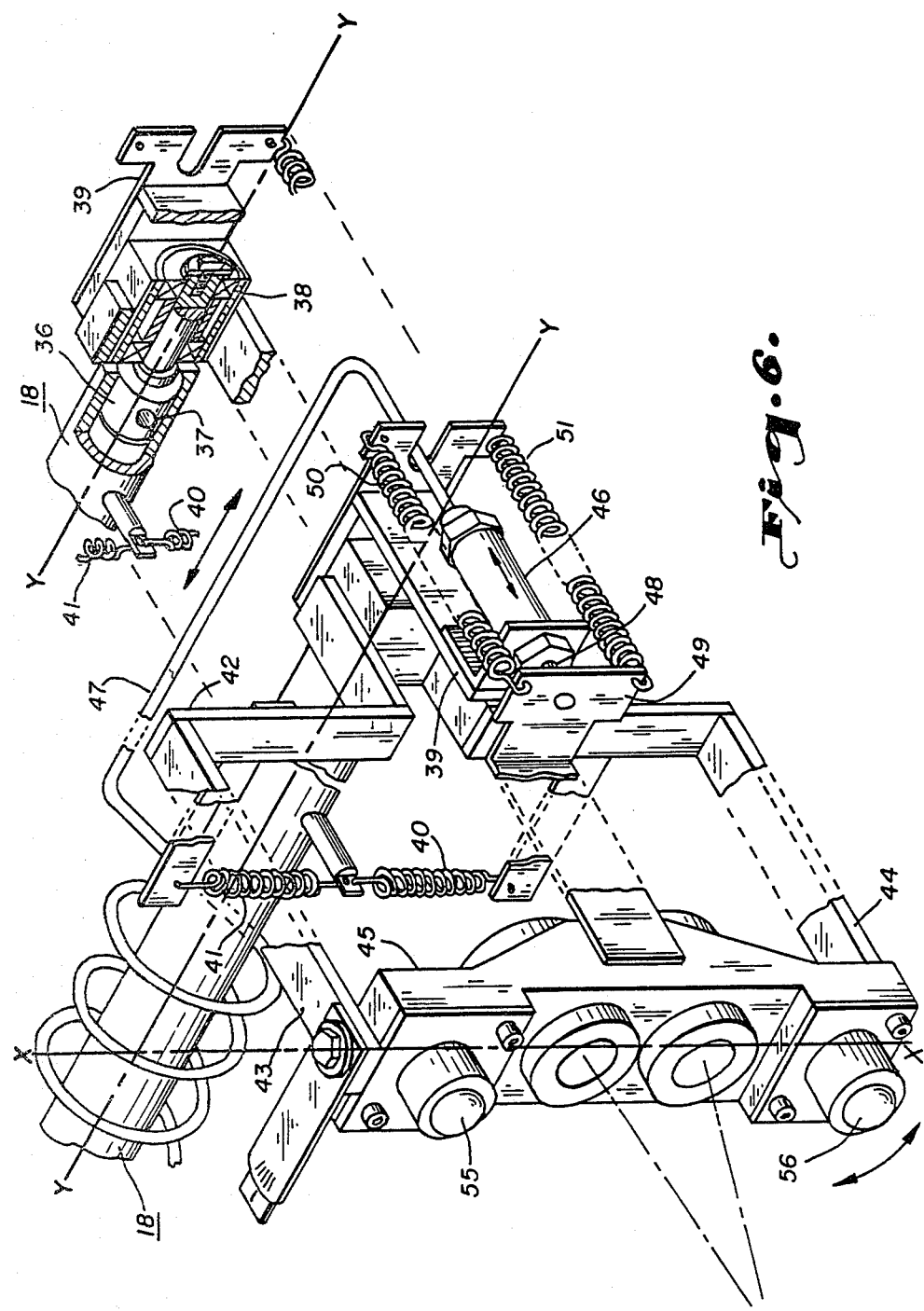
FIG. 6 is an exploded isometric of the structure on the outer reach of each radially deployable arm.

FIG. 6—Station 16 Structure

FIG. 6 is an elaborate and detailed disclosure of the structure mounted on the outer ends of arms 17 and 18. Thus, there are two such structures which are identical. These structures are identified on FIG. 4 as 15 and 16.

The purpose of these structures at 15 and 16 is to connect the probes to arms 17 and 18 and, hence, to the rest of the support system, such that the probes will have a controlled motion about axis X and a limited degree of freedom about axis Y.

Arm 18 has telescoped within it at its extreme outer end, bearing shaft 36. These members are pinned together at 37. The stations designated on FIG. 4 as 15 and 16 are free to pivot about axis Y, using bearings 38 to minimize friction. As mentioned in the foregoing paragraph, this is a limited freedom in that springs 40 and 41 extend from attachment to arm 18 to constantly urge 42, 43, 44 of the frame 39 to return to a mid-position in its arc of rotation. The purpose of this freedom to pivot is to allow sled 45 to ride on its spherical rollers 55 and 56 over irregularities that exist on the surface of weld body 11. This is termed "freedom" due to the fact that the sled pivots as it will, rather than from any system program.

Although frame 39, in its bearing mounting on the end of shaft 36, has a complex shape in its own right, it must be further considered to include sled bracket 42 and arms 43 and 44. The complex shapes of these structures, singly and together, can be readily traced by eye through an observation of the isometric convention of FIG. 6. At this point, the structures must be observed as a unit mounted on the end of shaft 36. It is in this framework that the slave actuator 46 of the hydraulic system is mounted. This actuator receives pressure signals from master actuator 29a. The master actuator is mechanically linked to cam followers 28 and 29 which, in turn, rise and fall on cam 26. Thus, the ultrasonic probes are moved through predetermined angles of direction about axis X. This motion, therefore, is relative to the shape of cam surface 27. This, then, is the "controlled motion" mentioned in the foregoing.

Arms 43 and 44 of sled bracket 42 extend parallel to each other to support sled 45 through pivots, thus defining axis X. The control of the pivoting of sled 45 about axis X between its support on the outer ends of the arms 43, 44 is the objective of the present invention. All that remains is to connect sled 45 to the hydraulic system so that the sled may be positioned by the edge 27 of cam 26.

Direct power for the pivoting of sled 45 is provided by the hydraulic fluid conducted to slave actuator 46. Slave actuator 46 is mounted securely to frame 39 and is connected to conduit 47 which extends to the master cylinder 29a which is linked to cam follower 29. Therefore, movement of follower 29 by the rise and fall of cam 26 establishes the varying hydraulic pressure conducted and applied to slave actuator 46, resulting in the movement of piston rod 48 out of actuator 46. The end of piston rod 48 bears upon the surface of bracket 49 which is simply an extension of sled 45 to which it is connected. Springs 50 and 51 are connected between frame 39 and bracket 49 to urge bracket 49 against the end of piston rod 48 of slave actuator 46. Therefore, increased pressure in the hydraulic system will move bracket 49 in one direction, and a decrease in this pressure will enable springs 50, 51 to move bracket 49 in the opposite direction. For each value of the hydraulic pressure in opposition to the springs 50, 51, there will be determined a position of bracket 49 and its sled 45.

All that remains is to determine the angle desired to pivot sled 45 and its ultrasonic probes to carry out the scan desired of weld body 11. The edge 27 of cam 26 is cut to pivot sled 45 through the required angle as the entire assembly is rotated and the manifestation obtained from the ultrasonic probes mounted on the sled 45 will provide the flaw information desired.

Conclusion

The present invention can be described as a manipulating device for precise directional control of an inspection tool. The use of the tool is to detect flaws. More specifically, the inspection tool is an ultrasonic transducer with an output which must be directed at an angle with the centerline of the weld body penetrated by the output. With the centerline of the weld body deviating from a plane, the transducer carried over the surface of the weld body and in alignment with the centerline of the body, must be continuously repositioned to maintain the required output angle to carry out the required scan of the weld body. The present invention can be described as a device which embodies a programming cam and a force system which will automatically alter the scanning angle of an ultrasonic transducer to properly follow the varying contour of a weld body.

Although repetitious, the description of this important relationship will again be stated. The inspection tool is an ultrasonic transducer with an output beam that must be directed at a specific angle relative to the geometric shape of the weld body. Due to the fact that this geometric shape presents a varying aspect, depending upon angular location about axis Z it follows, the angle of the output beam must be continuously varied to carry out the required scan of the weld body.

Although not necessarily limited to inspecting a circular weld configuration by transducers mounted on the ends of arms which sweep through a circular path, the invention finds first reduction to practice in this arrangement. Therefore, the embodiment of the invention is first defined in the environment where the transducer is mounted on the end of an arm pivoting about a centerline, or axis Z, approximately normal to the curved plane of the weld body to be inspected. A cam is mounted on this centerline, or axis, in a fixed position. A power system is extended from the cam radially outward along a pair of opposing arms, the ends of which each mount a transducer. The profile of the cam is maintained in contact with one end of the power system to develop positions for the second end of the power system at the outer end of the pivoting arm where the transducer is brought into contact with the power system. Therefore, as the arm is rotated about axis Z, the master actuator of the power system is forced by the profile of the cam to generate positions of the slave actuator at the outer end of the arm. The slave actuator contacts the transducer structure and pivots the structure in accordance with the cam profile to continuously readjust the position of the transducer and maintain the required angle of transducer output with the geometry of the weld body.

From the foregoing, it will be seen that this invention is one well adapted to attain all of the ends and objects hereinabove set forth, together with other advantages which are obvious and inherent to the apparatus.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawings is to be interpreted as illustrative and not in a limiting sense.

We claim:

1. In a weld body inspection tool which positions an ultrasonic detector from the centerline of a cylindrical nozzle joined to a cylindrical aperture in the side of a nuclear reactor vessel by moving the detector connected to the outer end of an extensible arm over the surface of the weld body,
   a cam fixedly mounted at the center of arm rotation,
   a hydraulic closed loop power system connected between the cam and the ultrasonic transducer mounted at the outer end of the extensible arm to control the direction of the output of the ultrasonic transducer as the arm pivots to maintain a predetermined relationship of the ultrasonic transducer output to the weld geometric shape,
   and means connected to the ultrasonic transducer to manifest the reflection of the transducer output in detection of imperfections in the weld body.

2. The inspection tool of claim 1, including,
   a spring member connected to the ultrasonic detector to urge the detector in one direction of movement in opposition to the power of the hydraulic system.

3. An inspection tool for detecting weld integrity, including, an ultrasonic transducer for establishing and sensing reflections of output of ultrasonic energy directed into a weld body,
   a sled on which the ultrasonic transducer is mounted,
   an arm radially extensible and pivotable about an axis and connected to the sled by its outer end to carry the transducer over the surface of a circular weld body,
   power means connected to the sled with which the sled is automatically moved in directing the transducer output through a predetermined angle relative to the geometric shape of the weld body,
   a cam fixedly mounted at the axis of arm pivoting and having a profile in contact with the power means to actuate the power means to automatically shift the position of the sled as the arm is pivoted and direct the output of the transducer in a predetermined relationship to the geometric shape of the weld body,
   and means for manifesting the output of the ultrasonic transducer in terms of weld integrity.

4. The inspection tool of claim 3, in which,
   the power system is a closed loop hydraulic master actuator/slave actuator system controlled at the master actuator by contact with the cam profile about the axis of arm pivoting the contacting the sled by the slave actuator at the outer end of the pivoting arms.

5. Apparatus for carrying an ultrasonic weld flaw detector over the surface of a circular weld body, including,
   support structure on which is mounted a mechanical arm radially extensible and pivotable about the normal axis of the circular weld body,
   a weld body to be inspected for flaws arranged about the center of arm pivoting,
   means for pivoting the mechanical arm,
   means for radially extending and retracting the length of the mechanical arm about the pivot axis,
   an ultrasonic flaw detecting transducer mounted on the outer end of the pivoted arm and movable to vary the angle of the transducer output relative to the varying aspect of the weld body geometric shape, power means extending from the axis of rotation into contact with the transducer on the outer end of the arm for moving the transducer, a cam fixedly mounted at the axis of rotation and in contact with the power means to control the positioning of the transducer by the power means in accordance with the predetermined cam profile as the arm is pivoted, and means connected to the transducer to manifest flaws sensed by the transducer in its travel over the surface of the weld body as the transducer is actuated by the power means.

6. The carrying apparatus of claim 5 in which the power means includes, a master actuator contacting the profile of the cam at the axis of rotation, a slave actuator mounted at the outer end of the arm contacting the transducer, and a closed conduit of hydraulic fluid connecting the master actuator and the slave actuator.

* * * * *